(12) United States Patent
Shudo et al.

(10) Patent No.: US 6,761,900 B2
(45) Date of Patent: Jul. 13, 2004

(54) TOPICAL PATCH PREPARATION CONTAINING A DELAYED-TYPE HYPERSENSITIVITY INDUCER AND METHODS FOR USING THE SAME

(75) Inventors: Jutaro Shudo, San Jose, CA (US); Ichiro Mori, San Jose, CA (US)

(73) Assignee: Teikoku Pharma USA, Inc., Campbell, CA (US)

( * ) Notice: Subject to any disclaimer, the term of this patent is extended or adjusted under 35 U.S.C. 154(b) by 0 days.

(21) Appl. No.: 10/080,526

(22) Filed: Feb. 21, 2002

(65) Prior Publication Data

US 2002/0176886 A1 Nov. 28, 2002

Related U.S. Application Data

(60) Provisional application No. 60/275,213, filed on Mar. 12, 2001.

(51) Int. Cl.$^7$ .......................... A61F 13/02; A61F 15/16; A61F 13/00
(52) U.S. Cl. .......................... 424/448; 424/449; 424/443
(58) Field of Search .............................. 424/448, 449, 424/443

(56) References Cited

U.S. PATENT DOCUMENTS

| | | | |
|---|---|---|---|
| 4,129,647 A | | 12/1978 | Klein |
| 4,214,592 A | | 7/1980 | Jacquet et al. |
| 5,476,664 A | * | 12/1995 | Robinson et al. ........... 424/443 |
| 5,846,559 A | * | 12/1998 | Hopp ..................... 424/448 |
| 5,891,920 A | * | 4/1999 | Hirano et al. ............... 514/629 |

FOREIGN PATENT DOCUMENTS

| | | |
|---|---|---|
| EP | 0782861 A | 7/1997 |
| EP | 1029542 A | 8/2000 |
| EP | 1170020 A | 1/2002 |

OTHER PUBLICATIONS

Stricker et al. "Decrease in viral load associated with topical dinitrochlorobenzene therapy in HIV disease" *Res Virol* (1997) 148:343–348.

Oracion et al. "DNCB treatment of HIV–infected patients leads to beneficial immunologic outcomes, reduced viral load, and improved measures of quality–of–life" *J. Invest Deermatol.* (1998) 110:476.

Stricker et al. Dendritic cells and dinitrochlorobenzene (DNCB): A new treatment approach to AIDS *Immunol Letter* (1991) 29:191–196.

Stricker et al. "Pilot study of topical dinitrochlorobenzene (DNCB) in human immuno deficiency virus infection" *Immunol Letters*, (1993) 36:1–6.

Stricker et al. "Tropical dinitrochlorobenzene in HIV disease"*J. Am. Acad Dermatol* (1993) 28:796–797.

Stricker et al. Clinical and immunologic evaluation of HIV–infected patients treated with dinitrochlorobenzene (DNCB). *J. Am. Acad Dermatol* (1994) 31:462–466.

(List continued on next page.)

*Primary Examiner*—Gollamudi S. Kishore
*Assistant Examiner*—Isis Ghali
(74) *Attorney, Agent, or Firm*—Bret E. Field; Bozicevic, Field & Francis LLP

(57) ABSTRACT

Topical patch preparations that contain a delayed-type hypersensitivity inducer, e.g., 1-dichloro-2,4-dinitrobenzene (DNCB), and methods for using the same are provided. The subject topical patch preparations are made up of an adhesive gel composition that is present on a support, where the adhesive gel composition includes the delayed-type hypersensitivity inducer, a water-soluble polymer gel, water and a water holding agent. In using the subject topical patch preparations, the topical patch preparations are applied to a skin surface of a subject and maintained at the site of application for a period of time sufficient for an effective amount of the delayed-type hypersensitivity inducer to be administered to the subject, where this maintenance period typically does not exceed about 60 minutes. The subject invention finds use in a variety of applications where the administration of a delayed-type hypersensitivity inducer is desired, and is particularly suited for use in the treatment of HIV associated disease conditions, e.g., AIDS.

18 Claims, 3 Drawing Sheets

OTHER PUBLICATIONS

Stricker et al. Improved results of delayed–type hypersensitivity skin testing in HIV–infected patients treated with topical dinitrochlorobenzene (DNCB). *J. Acad Dermatol.* (1995) 33:608–611.

Stricker and Goldberg "Safety of topical dinitrochlorbenzene Lancet" (1995) vol. 346 pp. 1293.

Stricker et al. "Improved results of delayed–type hypersensitivity skin testing in HIV–infected patients treated with topical dinitrochlorobenzene" *J Am Acad Dematol* (1996) 35:491–493.

Stricker et al. "Decrease in viral load associated with topical dinitrochlorobenzene therapy in HIV disease" *Res Virol* (1997) 148:343–348.

Traub et al. "Topical immune modulation with dinitrochlorobenzene (DNCB) in HIV disease: A controlled trial from Brazil" *Dermatology* (1997) 195:369–373.

Stricker et al. "Topical immune modulation (TIM): A novel approach to the immunotherapy of systemic disease" *Immunol Letters* (1997) 59:145–150.

Oracion et al. "DNCB treatment of HIV–infected patients leads to beneficial immunologic outcomes, reduced viral load, and improved measures of quality–of–life" *J. Invest Dermatol.* (199 ) 110:476.

* cited by examiner

TOPICAL PATCH PREPARATION CONTAINING A DELAYED-TYPE HYPERSENSITIVITY INDUCER AND METHODS FOR USING THE SAME

CROSS REFERENCE TO RELATED APPLICATIONS

Pursuant to 35 U.S.C. §119(e), this application claims priority to the filing date of the U.S. Provisional Patent Application Serial No. 60/275,213 filed Mar. 12, 2001; the disclosures of which are herein incorporated by reference.

INTRODUCTION

Field of the Invention

The field of this invention is delayed-type hypersensitivity inducing agents.

BACKGROUND OF THE INVENTION

The number of Human Immunodeficiency Virus (HIV) patients worldwide has been increasing rapidly in recent years, and is said to be approximately 33 million (WHO; end of 1998). Against this backdrop, there is a rush to develop a vaccine for HIV. However, but because of the mutation of the configuration of the virus following infection, a feature of HIV, an accurate vaccine has not yet been found. In addition, although many therapeutic medications for HIV have been developed, none completely cure HIV. Furthermore, current AIDS drugs (protease inhibitors, non-nucleoside reverse transcriptase inhibitors, nucleoside reverse transcriptase inhibitors, etc.) employ complex techniques. Long-term administration of these agents causes patients to suffer persistent adverse events, such as anemia, peripheral neuritis, pancreatitis, nausea, and headaches. Also, the possibility of long-term administration resulting in drug resistance cannot be ruled out. Yet another disadvantage of current treatment modalities is cost, in that current therapeutic medications for HIV are extremely expensive, often ranging between $15,000 to $20,000 per person per year, which necessarily limits patient access.

One type of agent that represents an effective alternative to current HIV treatment modalities is the delayed-type hypersensitivity (DTH) inducing agent, which type of agent has been researched as an immunomodulator that elicits immunological response in HIV patients by increasing the activity of the immune system cells in the body. Delayed-type hypersensitivity inducers are substances that induce Type 4 hypersensitivity when they come into contact with human skin, and they include trinitrobenzene sulfonic acid, picryl chloride(PC), 2,4-dinitrofluorobenzene(DNFB), and 1-chloro-2,4-dinitrobenzene (DNCB). Of these, DNCB has been widely used in the treatment of HIV and in immunological research, and the present invention focuses on DNCB as a DTH inducer in many embodiments, as described in greater detail below.

DNCB was discovered in Germany before World War II. Research conducted in the 1950s in the US demonstrated that DNCB is not carcinogenic. Later, in the 1970s, safety research was conducted in various types of animals. DNCB is generally known to be a powerful, delayed allergy-inducing skin irritant in humans, and is used in, among other things, immunological tests of skin diseases.

Research on DNCB therapy in HIV patients began slowly from the middle of the 1980s, and research on DNCB therapy in HIV patients was conducted in the first half of the 1990s, from which DNCB was claimed to be effective for treating HIV. However, this claim was not proved. In the latter half of the 1990s, the development of PCR analysis technology began to confirm the efficacy of DNCB in HIV patients. In addition, DNCB was also previously investigated as a possible treatment for cancer: tests were conducted in which DNCB was applied locally to induce a delayed allergic reaction and thereby utilize its immunity inducing capabilities. However, these findings have not been put to practical use. Furthermore, DNCB has been used in, among other things, the treatment of warts.

A method for using DNCB in HIV patients that has been employed in recent years has been to dissolve the DNCB in an acetone solvent and impregnate a gauze-like cloth with the resulting product and apply this to the skin. This topical preparation is then dried, covered and left to stand for several hours (typically at least 8 hours). This long application time means that an HIV patient would be restricted for at least 8 hours, a fairly long time, which would prevent that person from leading the same lifestyle as a healthy person.

There is considerable interest, therefore, in the development of a topical DTH inducing agent composition that could efficiently deliver an effective amount of a DTH inducing agent to a host in a short period of time.

Relevant Literature

References of interest include: Stricker et al. Dendritic cells and dinitrochlorobenzene (DNCB): A new treatment approach to AIDS. *Immunol Letters* 1991;29:191–196; Stricker et al. Pilot study of topical dinitrochlorobenzene (DNCB) in human immuno deficiency virus infection. *Immunol Letters* 1993;36:1–6; Stricker et al. Topical dinitrochlorobenzene in HIV disease. *J Am Acad Dermatol* 1993;28:796–797; Stricker et al. Clinical and immunologic evaluation of HIV-infected patients treated with dinitrochlorobenzene (DNCB). *J Am Acad Dermatol* 1994;31:462–466; Stricker R B, Goldberg B, Mills L B, Epstein W L. Improved results of delayed-type hypersensitivity skin testing in HIV-infected patients treated with topical dinitrochlorobenzene (DNCB). *J Am Acad Dermatol* 1995;33:608–611; Stricker & Goldberg. Safety of topical dinitrochlorobenzene. *Lancet* 1995;346:1293; Stricker et al. Improved results of delayed-type hypersensitivity skin testing in HIV-infected patients treated with topical dinitrochlorobenzene. *J Am Acad Dermatol* 1996;35:491–493; Stricker et al. Decrease in viral load associated with topical dinitrochlorobenzene therapy in HIV disease. *Res Virol* 1997;148:343–348; Traub et al. Topical immune modulation with dinitrochlorobenzene (DNCB) in HIV disease: A controlled trial from Brazil. *Dermatology* 1997;195:369–373; Stricker et al. Topical immune modulation (TIM): A novel approach to the immunotherapy of systemic disease. *Immunol Letters* 1997;59:145–150; Oracion et al. DNCB treatment of HIV-infected patients leads to beneficial immunologic outcomes, reduced viral load, and improved measures of quality-of-life. *J Invest Dermatol* 1998;110:476.

SUMMARY OF THE INVENTION

Topical patch preparations that contain a delayed-type hypersensitivity inducer, e.g., 1-dichloro-2,4-dinitrobenzene (DNCB), and methods for using the same are provided. The subject topical patch preparations are made up of an adhesive gel composition that is present on a support, where the adhesive gel composition includes the delayed-type hypersensitivity inducer, a water-soluble polymer gel, water and a water holding agent. In using the subject topical patch preparations, the topical patch preparations are applied to a skin surface of a subject and maintained at the site of application for a period of time sufficient for an effective amount of the delayed-type hypersensitivity inducer to be administered to the subject, where this maintenance period typically does not exceed about 60 minutes. The subject invention finds use in a variety of applications where the administration of a delayed-type hypersensitivity inducer is desired, and is particularly suited for use in the treatment of HIV associated disease conditions, e.g., AIDS.

DESCRIPTION OF THE SPECIFIC EMBODIMENTS

Topical patch preparations that contain a delayed-type hypersensitivity inducer, e.g., 1-dichloro-2,4-dinitrobenzene (DNCB), and methods for using the same are provided. The subject topical patch preparations are made up of an adhesive gel composition that is present on a support, where the adhesive gel composition includes the delayed-type hypersensitivity inducer, a water-soluble polymer gel, water and a water holding agent. In using the subject topical patch preparations, the topical patch preparations are applied to a skin surface of a subject and maintained at the site of application for a period of time sufficient for an effective amount of the delayed-type hypersensitivity inducer to be administered to the subject, where this maintenance period typically does not exceed about 60 minutes. The subject invention finds use in a variety of applications where the administration of a delayed-type hypersensitivity inducer is desired, and is particularly suited for use in the treatment of HIV associated disease conditions, e.g., AIDS. In further describing the subject invention, the topical patch preparations are described first in greater detail, followed by a review of representative applications in which the subject topical patch preparations find use.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

Topical Patch Preparations

Figure 1:
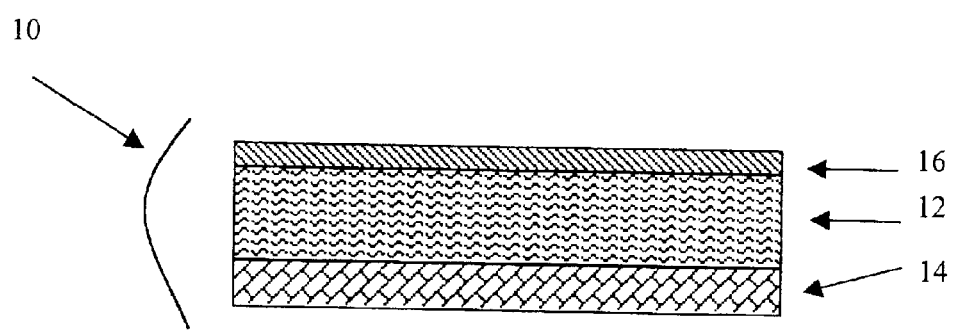
FIG. 1 provides a cross-sectional view of a topical patch preparation according to the invention.

As summarized above, the subject invention is directed to topical patch preparations of a delayed-type hypersensitivity inducer agent. The topical patch preparations of the subject invention are characterized by having an effective amount of the delayed type hypersensitivity inducer agent present in a gel adhesive base. FIG. 1 provides a representation of a topical patch preparation described according to the subject invention. As can be seen in FIG. 1, this representative topical patch preparation 10 contains a gel adhesive base 12 present on a support 14. Each of these components is now described in greater detail.

The gel adhesive base which serves as the delayed-type hypersensitivity inducer retaining layer, is made up of the delayed-type hypersensitivity inducer that is present in, e.g., dissolved in or dispersed in, and adhesive gel base. By "delayed-type hypersensitivity (DTH) inducers" is meant an immunomodulator that elicits immunological response in a subject, such as HIV patients, by increasing the activity of the immune system cells in the body. Delayed-type hypersensitivity inducers are substances that induce Type 4 hypersensitivity when they come into contact with human skin, and they include, but are not limited to: trinitrobenzene sulfonic acid, picryl chloride (PC), 2,4-dinitrofluorobenzene (DNFB), and 1-chloro-2,4-nitrobenzene (DNCB). In many embodiments, the delayed-type hypersensitivity inducer is DNCB.

The amount of DTH inducer that is present in the adhesive gel base is an amount sufficient to administer to a subject an effective amount of the agent when applied to a skin surface of the subject, as described in greater detail below. In many embodiments, the amount of DTH inducer present in the adhesive gel base ranges from about 0.01 to 10.0% (w/w), sometimes from about 0.05 to 10.0% (w/w), usually from about 0.1 to 5.0% (w/w) and more usually from about 0.2 to 3.0% (w/w).

The adhesive gel base that includes the DTH inducer, as described above, is made up of a water-soluble high molecular weight substance, water and a water retaining agent. In certain embodiments, the adhesive gel base may further include a cosolvent, e.g., an organic cosolvent. Each of these components is now described separately in greater detail.

Water-soluble high molecular weight substances of interest include water-soluble polymers, where polymers of interest include, but are not limited to: gelatin, starch, agar, mannan, alginic acid, polyacrylic acid, polyacrylate, dextrin, methylcellulose, sodium methylcellulose, hydroxypropylcellulose, sodium carboxymethylcellulose, cellulose gum, carboxyvinyl polymer, polyvinyl alcohol, polyvinylpyrrolidone, Arabia gum, acacia, tragacanth gum, karaya gum, and starch acrylate copolymer or other starch sodium acrylate graft copolymers. Metallic salts of these, as well as the products of cross-linking these by means of organic or inorganic cross-linking agents, are also of interest. These water-soluble polymers can be used to bring out the properties and characteristics of the other starting materials used in the adhesive gel composition, and in practice can be used alone or in combinations of 2 or more. The amount of water soluble high molecular weight substance(s) present in the adhesive gel base generally ranges from about 0.5 to 20, usually from a bout 2 to 20% (w/w).

While any convenient water may be employed as the water component, of interest are distilled water or ion-exchange water or the like, which is preferred in many embodiments of the subject invention. The amount of water present in the gel adhesive is sufficient to impart the desired physical properties to the gel adhesive, and to improve the swelling of the horny or keratinized layer of the skin to thereby improve the permeability or penetration of the DTH inducing agent(s), where the amount of water in the gel composition generally ranges from about 10 to 80%, usually from about 30 to 60% (w/w).

The water-retaining agent or water-holding agent of the subject adhesive gel compositions is any agent that is capable of at least diminishing the volatilization of water contained in the adhesive gel base so that the water content in the adhesive gel base is maintained at least a substantially constant, if not constant, level during storage and use of the preparation. One or more water-retaining agents may be employed in the subject compositions, where the amount of water-retaining agent present in the adhesive gel base generally ranges from about 1 to 70%, more preferably 10 to 60% by weight. Examples of suitable water-retaining or water-holding agents include, but are not limited to: 1 or more types of polyvalent or polyhydric or sugars or alcohols, such as glycerin, sorbitol, propylene glycol, diethylene glycol, 1,3-butylene glycol, and ethylene glycol, and the like.

In addition, the subject gel base compositions may also include a cosolvent, where the cosolvent is generally an organic cosolvent. Examples of DNCB cosolvents of interest include, but are not limited to, n-methyl-2-pyrrolidone, crotamiton, ethyl alcohol, methyl alcohol, polyethylene glycol (e.g., low molecular weight polyethylene glycol, such as PEG 600 or lower, e.g., 500, 400, 300, 200, 100 etc and blends thereof, and acetone, where n-methyl-2-pyrrolidone, polyethylene glycol and crotamiton are of particular interest. The cosolvent may be made up of a simple component or be incombination of two or more components.

Furthermore, in addition to the aforementioned ingredients, various additives that are used in ordinary topical water-soluble patch preparations may also be suitably compounded as needed, including inorganic substances such as kaolin, bentonite, and titanium dioxide; preservatives such as paraben; anionic, cationic, and nonionic surfactants; metallic aluminum crosslinking agents such as aluminum chloride, dried aluminum hydroxide gel, and dihydroxyaluminum aminoacetate; oils such as jojoba oil and castor oil; chelating agents such as EDTA; pH regulators such as malic acid, tartaric acid, and diisopropanolamine; alcohols such as ethanol; moisture retaining agents such as hyaluronic acid, aloe extract, and urea; and other perfumes and coloring agents.

The pH of the gel base composition typically is one that lies in a physiologically acceptable range, where the pH typically ranges from about 4.0 to 7.0 and more typically ranges from about 4.0 to 6.0.

As mentioned above, the adhesive gel composition containing the one or more active ingredients is typically present on a support or backing. The support is generally made of a flexible material which is capable of fitting in the movement of human body and includes, for example, various non-woven fabrics, woven fabrics, spandex, flannel, or a laminate of these materials with polyethylene film, polyethylene glycol terephthalate film, polyvinyl chloride film, ethylene-vinyl acetate copolymer film, polyurethane film, and the like.

In addition to the adhesive gel composition and the support layer, the subject topical patches may also include a release film 16 on the surface of the gel layer opposite the backing that provides for protection of the gel layer from the environment. The release film may be any convenient material, where representative release films include polyesters, such as PET or PP, and the like.

In many embodiments, the patch is present in a sealed package. Generally, the sealed package is fabricated from a packaging material that includes a layer made out of a material capable of preventing passage of moisture, oxygen and other agents, i.e., the package includes in a moisture/oxygen barrier material. Any suitable barrier material may be employed, where barrier materials of interest include metallic layers, e.g., aluminum, where in many embodiments, the barrier layer is an aluminum layer. This barrier layer has a thickness sufficient to provide for the barrier function, where the thickness typically ranges from about 5 to 15, usually from about 6 to 10 $\mu$m. In many embodiments, the package is a laminate of the barrier layer in combination with one or more additional layers, e.g., polymeric layers, paper layers, etc. A representative aluminum containing package that may be used with the subject patch preparations is sold by Dainippon Printing Co., Ltd. (Kyoto, Japan).

The topical patch preparations may be fabricated using any convenient protocol. One convenient protocol for fabrication of the subject patches includes preparing a gel adhesive paste through the uniform mixing of the aforementioned ingredients and then coating the paste onto the support, followed by cutting of the resultant product to the specified size to obtain the desired topical patch preparation. The resultant topical patch preparation is then heat-sealed, typically several sheets to a package, using a packaging material containing an aluminum layer, as described supra, to obtain the sealed topical patch. For a more detailed description of the fabrication protocol, see U.S. Pat. No. 5,827,529; the disclosure of which is herein incorporated by reference.

Figure 2:
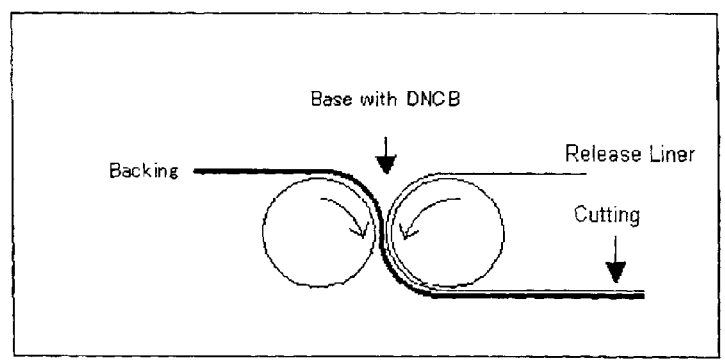
FIGS. 2 and 3 provide schematic representations of the manufacturing process for topical patch preparations of the invention.

In a representative fabrication protocol, the base used in the present invention is produced by using a mixer to uniformly blend the aforementioned ingredients by means of any convenient protocol into a paste, which is then spread by means of a spreader onto a backing or support material. As indicated above, the support material may be, for example, paper, or a woven or nonwoven cloth made of PET or PP or some other polyester fiber. For protection, the surface thereof is then covered with a release film of a polyester such as PET or PP. These steps are illustrated in FIG. 2.

Figure 3:
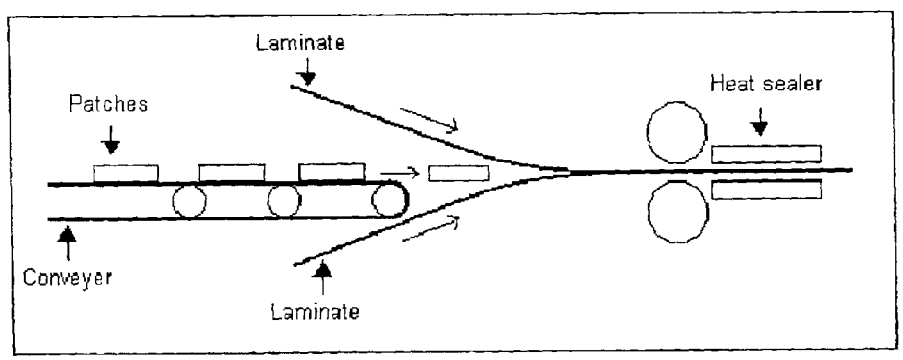

The resulting product is then cut to the specified size to obtain the desired topical patch preparation composition. The shape of the patch may vary, where representative shapes include square, rectangle, oval, circle, etc. The size of the patch may also vary, where in many embodiments the size ranges from about 1 to 200 $cm^2$, and in many embodiments from about 10 to 100 $cm^2$, usually from about 20 to 50 $cm^2$, e.g., 25 $cm^2$. The weight of the base in the final topical patch should be 300 to 1500 $g/m^2$, and preferably 600 to 1000 $g/m^2$. This water-soluble topical patch preparation is then packaged by means of a heat seal in a packaging material that includes a layer of aluminum to obtain the final product, as shown in FIG. 3.

It should be noted that the above manufacturing protocols are merely representative. Any convenient protocol that is capable of producing the subject topical patch preparations, as described above, may be employed.

Methods of Using Patch Preparations

The subject patch preparations find use in the topical delivery of DTH inducing agents, e.g., DNCB, to a host. By "topical delivery" is meant delivery via absorption through the skin. In using the subject topical patch preparations to topically administer a DTH inducing agent to the host, the topical preparation is applied to a skin surface and maintained at the site of application for a period of time sufficient for the desired amount of DTH inducing agent to be delivered to the host. In many embodiments, the period of time required to deliver the desired amount of agent is short, generally not exceeding about 60 minutes, usually not exceeding about 30 minutes and in many embodiments not exceeding about 15 minutes. However, the period of time during which the preparation is maintained at the application site is, in many embodiments, at least about 1 minute, usually at least about 3 minutes and more usually at least about 5 minutes.

The patch may be administered to any convenient topical site. Topical sites of interest include, but are not limited to: arms, leg, torso, etc. The surface area that is covered by the topical patch preparation following application must be sufficient to provide for the desired amount of agent administration, and in many embodiments ranges from about 1 to 200 cm$^2$, and in many embodiments from about 10 to 100 cm$^2$, usually from about 20 to 50 cm$^2$, e.g., 25 cm$^2$. In practicing the subject methods, a topical patch may be applied a single time or a plurality of times over a given time period, e.g., the course of the disease condition being treated, where the dosing schedule when a plurality of patches are administered over a given time period may be daily, weekly, biweekly, monthly, etc.

Utility

The above described patches and methods find use in any application in which the administration of an DTH inducing agent to a host is desired. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

In many embodiments, the subject methods find use in the treatment of a disease condition. By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as viral load or side effects associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition. As such, treatment includes both curing and managing a disease condition.

In many embodiments, the disease condition that is treated according to the subject methods is one that is a chronic disease. Chronic diseases of interest include, but are not limited to: chronic fatigue syndrome, systemic lupus erythematosus, leprosy, leishmaniasis, diseases associated with the presence of intracellular pathogenic agents (e.g., viruses, bacteria), such as cytomegalovirus, Candida, Cryptococcus, Penumocystis carinii, and the like.

Of particular interest is the use of the subject methods in the treatment, e.g., management, of immunocompromising disease conditions, and particularly HIV associated disease conditions, e.g., AIDS. Treatment in the context of HIV associated diseases means improvement of quality of life, e.g., via reduction in one or more symptoms, the occurrence of opportunistic infections, etc. In terms of quantifiable parameters associated with HIV disease conditions, the subject invention finds use in reducing viral load and/or increasing the population of natural killer cells, while varying the population of at least one of CD4 cells and CD8 cells. Such changes in quantifiable parameters are achievable with application times that do not exceed 15 minutes in length.

Kits

Also provided are kits, where the subject kits at least include one or more DTH inducing agent topical patch preparations, as described above. The subject topical patch preparations in the kits may be present in a package, as described supra. The topical patches of the kits are typically present in individual pouches or analogous containers, to preserve the composition of the patches until use. The subject kits also generally include instructions for how to use the patches in DTH inducing agent delivery to a host where the instructions typically include information about where to apply the patch, dosing schedules etc. In certain embodiments, the subject kits include instructions on how to use to the patched to treat a particular disease condition with a DTH inducing agent. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g. CD-ROM, diskette, etc.

The following practical and comparative examples are offered by way of illustration and not by way of limitation.

EXAMPLES

Practical and comparative examples are given below, but the manufacturing method is not limited thereby.

I. Preparation of Topical Patches

Practical Examples

A water-soluble polymer topical patch preparation in which DNCB has been compounded in an amount of 2%. 2% DNCB is dissolved in n-methyl-2-pyrrolidone, after which the ingredients are blended into uniformity and adjusted into a paste, which is then spread onto a PET nonwoven cloth to a weight of 850 g/m$^2$; the resulting product is then laminated with a PP film and then cut into 5 cm squares. Finally, each individual DNCB patch is heat-sealed in packaging material containing aluminum foil to obtain the finished product. See FIGS. 2 and 3.

Placebo—A water-soluble polymer topical patch preparation in which water was used in place of the DNCB in the practical example. The ingredients are blended into uniformity and adjusted into a paste, which is then spread onto a PET nonwoven cloth to a weight of 850 g/m$^2$; the resulting product is then laminated with a PP film and then cut into 5 cm squares. Finally, each individual placebo patch is heat-sealed in packaging material containing aluminum foil to obtain the finished product. See FIGS. 2 and 3. Table 1 summarizes the content of the practical and placebo compositions.

TABLE 1

| Starting Material | Practical Example | Placebo |
|---|---|---|
| DNCB | 2.0 | — |
| Water | 49.525 | 51.525 |
| EDTA | 0.1 | 0.1 |
| Methylparaben | 0.15 | 0.15 |
| Tartaric acid | 0.7 | 0.7 |
| Sodium polyacrylate | 5.0 | 5.0 |
| Polyacrylic acid | 4.0 | 4.0 |
| n-methyl-2-pyrrolidone | 2.0 | 2.0 |
| Castor oil | 2.0 | 2.0 |
| Aluminum hydroxide | 0.025 | 0.025 |
| Cellulose gum | 4.0 | 4.0 |
| Glycerin | 20.0 | 20.0 |

TABLE 1-continued

| Starting Material | Practical Example | Placebo |
|---|---|---|
| Sorbitol | 10.0 | 10.0 |
| Kaolin | 0.5 | 0.5 |
| Total | 100.000 | 100.000 |
| PH | 4.5–5.0 | 4.5–5.0 |

*: All values are expressed in terms of % (w/w).

II. Stability Data

Stability data on the DNCB content in the practical example. The experiment was conducted in an environment of 25° C. and 60% humidity. The results are shown in a comparison with the initial value, which was taken to be 100% and are provided in Table 2.

TABLE 2

|  | Initially | After 1 month | After 3 months | After 6 months | After 9 months |
|---|---|---|---|---|---|
| DNCB content | 100% | 99.5% | 99.2% | 99.0% | 99.1% |

III. Discoloration Test

We measured the degree of discoloration for the stability of the DNCB water-soluble topical preparation in the practical example. The experiment was conducted in an environment of 25° C. and 60% humidity. The results are shown in terms of the degree of discoloration relative to the initial value and are provided in Table 3.

TABLE 3

|  | Initially | After 1 month | After 3 months | After 6 months | After 9 months |
|---|---|---|---|---|---|
| Degree of discoloration | − | + | + | + | + |

Considerable difference: 3+
Visible difference: 2+
Slight difference: +
No change: −

IV. Activity Assay

We applied the DNCB water-soluble topical patch preparation of the practical example to HIV patient volunteers to investigate its efficacy for HIV. We used the placebo water-soluble topical patch preparation for comparison.

We applied the patch preparation to the upper extremity of 5 volunteers for 8 hours (1 patient), 4 hours (1 patient), and 15 minutes (3 patients), and after 1 week collected and analyzed their blood. Viral Load (VL) measurements were taken by means of ultrasensitive HIV-1 RNA PCR analysis.

The results are shown below in Table 4.

TABLE 4

|  | Application Time | Skin irritation | CD4 Pre | CD4 Post | CD8 Pre | CD8 Post | NK Pre | NK Post | VL Pre | VL Post |
|---|---|---|---|---|---|---|---|---|---|---|
| Patient 1 | 8 hours | G4 | 110 | 129 | 622 | 632 | 60 | 32 | 45930 | 71676 |
| Patient 2 | 4 hours | G3 | 257 | 248 | 1379 | 1562 | 70 | 74 | <20 | <20 |
| Patient 3 | 15 minutes | G0 | 107 | 199 | 426 | 637 | 67 | 82 | 85615 | 1188 |
| Patient 4 | 15 minutes | G0 | 253 | 226 | 747 | 767 | 24 | 34 | 23385 | 5720 |
| Patient 5 | 15 minutes | G0 | 14 | 6 | 826 | 303 | 14 | 50 | 581655 | 68144 |

*1: CD4 & CD8; T-Cell Subsets: NK, Natural Killer Cell: VL: Viral Load (RNA PCR)
*2: Skin Reaction Grade
Grade 4 (G4): Erythema, blistering and bulla formation
Grade 3 (G3): Erythema, blistering; no bulla
Grade 2 (G2): Erythema covering entire patch area; no blistering
Grade 1 (G1): Mild erythema covering less than entire patch area
Grade 0 (G0): Minimal or no reaction at patch site

V. DISCUSSION

Based on Tables 2 and 3, the DNCB in the water-soluble patch preparation is stable; discoloration was within a usable range, and practicality was sufficient. Table 4 shows that, in Patient 1, when the DNCB water-soluble patch preparation was applied for a long period of time (8 hours), considerable skin irritation occurred; CD4 and CD8 counts increased, but NK decreased, and VL increased. In Patient 2, the degree of skin irritation was less than for Patient 1. The NK count increased somewhat, and no significant change was seen in VL. For Patients 3 through 5, the time of application was short (15 minutes), and there was no skin irritation. However, the CD4 and CD8 counts exhibited changes, the NK count clearly increased, and the VL decreased dramatically, clearly demonstrating the suppression of the HIV blood concentration. Since DNCB immunological activation contributes to the increase in NK cells, it is also contributes to the decreased VL. Based on this information, it is meaningless to apply the DNCB water-soluble patch preparation for a long period of time; simply applying it to the skin for a short period (about 15 minutes) is extremely effective versus HIV, and is clearly practical. In addition, we simultaneously conducted a study in which a placebo was applied: there was no skin irritation, and absolutely no effect on HIV. This reconfirmed the clear effect of DNCB. Furthermore, when using the patch, simply applying it to the skin for a short period of time allows AIDS to be treated without a change in the lifestyle of the patient, who is therefore able to lead exactly the same lifestyle as a healthy person. In addition, concomitant use with other HIV therapeutic medications is also quite possible. Research has been conducted for some time into the adverse events of DNCB, and there have not been any reports to date of cases of life-threatening adverse events, such as carcinogenicity. Moreover, the DNCB water-soluble topical patch preparation of the present invention is only applied once a week, so treatment is possible at a cost of approximately $300 per person per year, making it cheaper than other HIV therapeutic medications and making it possible to use it in developing countries as well.

It is evident from the above results and discussion that the subject invention provides for a number of advantages in the delivery of DTH inducing agents. The subject topical preparations are efficient and effective delivery vehicles for administration of a DTH inducing agent to a subject, and need only be applied for a short period of time in order to provide the agent administration. Furthermore, the subject topical patch preparations are 25° C. storage stable. The subject preparations represent a low cost way of treating many disease conditions, including AIDS. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A topical patch preparation comprising:
   (a) an adhesive gel composition having a pH ranging from about 4.0 to 7.0 and comprising:
      (i) DNCB in an amount ranging from about 0.01 to 10.0% (w/w);
      (ii) a water-soluble polymer gel;
      (iii) water in an amount ranging from about 10 to 80% (w/w);
      (iv) a ionic is aluminum crosslinking agent; and
      (v) a water retaining agent; and
   (b) a support.

2. The topical patch preparation according to claim 1 wherein said DNCB is present in an amount ranging from about 0.1 to 5.0% (w/w).

3. The topical patch preparation according to claim 2 wherein said DNCB is present in an amount ranging from about 0.2 to 3.0% (w/w).

4. The topical patch preparation according to claim 1, wherein said water is present in an amount ranging from about 20 to 70% (w/w).

5. The topical patch preparation according to claim 4, wherein said water is present in an amount ranging from about 30 to 60% (w/w).

6. The topical patch preparation according to claim 1, wherein said pH ranges from about 4.0 to 6.0.

7. W The topical patch preparation according to claim 6, wherein said adhesive gel composition further comprises an organic solvent.

8. The topical patch preparation according to claim 7, wherein said organic solvent is selected from the group consisting of n-methyl-2-pyrrolidone, polyethylene glycol, and crotamiton and combinations thereof.

9. A topical patch preparation comprising:
   (a) an adhesive gel composition having a pH ranging from about 4.0 to 6.0 and comprising:
      (i) DNCB in an amount ranging from about 0.2 to 3.0% (w/w);
      (ii) a water-soluble polymer gel;
      (iii) water in an amount ranging from about 30 to 60% (w/w);
      (iv) a water retaining agent;
      (v) an organic cosolvent selected from the group consisting of n-methyl-2-pyrrolidone, polyethylene glycol and crotamiton and combinations thereof; and
      (vi) a ionic aluminum crosslinking agent; and
   (b) a support.

10. A topical patch preparation comprising:
    (a) a release film;
    (b) an adhesive gel composition having a pH ranging from about 4.0 to 7.0 and comprising:
       (i) DNCB in an amount ranging from about 0.01 to 10.0% (w/w);
       (ii) a water-soluble polymer gel;
       (iii) water in an amount ranging from about 10 to 80% (w/w);
       (iv) a water retaining agent; and
       (v) a ionic aluminum crosslinking agent; and
    (c) a support.

11. The topical patch preparation according to claim 10, wherein said DNCB is present in an amount ranging from about 0.1 to 5.0% (w/w).

12. The topical patch preparation according to claim 11, wherein said DNCB is present in an amount ranging from about 0.2 to 3.0% (w/w).

13. The topical patch preparation according to claim 10, wherein said water is present in an amount ranging from about 20 to 70% (w/w).

14. The topical patch preparation according to claim 13, wherein said water is present in an amount ranging from about 30 to 60% (w/w).

15. The topical patch preparation according to claim 10, wherein said pH ranges from about 4.0 to 6.0.

16. The topical patch preparation according to claim 15, wherein said adhesive gel composition further comprises an organic solvent.

17. The topical patch preparation according to claim 16, wherein said organic solvent is selected from the group consisting of n-methyl-2-pyrrolidone, polyethylene glycol, and crotamiton and combinations thereof.

18. A topical patch preparation comprising:
    (a) a release film;
    (b) an adhesive gel composition having a pH ranging from about 4.0 to 6.0 and comprising:
       (i) DNCB in an amount ranging from about 0.2 to 3.0% (w/w);
       (ii) a water-soluble polymer gel;
       (iii) water in an amount ranging from about 30 to 60% (w/w);
       (iv) a water retaining agent;
       (v) an organic cosolvent selected from the group consisting of n-methyl-2-pyrrolidone, polyethylene glycol and crotamiton and combinations thereof; and
       (v) a ionic aluminum crosslinking agent; and
    (c) a support.

* * * * *

UNITED STATES PATENT AND TRADEMARK OFFICE
CERTIFICATE OF CORRECTION

PATENT NO.    : 6,761,900 B2
DATED         : July 13, 2004
INVENTOR(S)   : Jutaro Shudo et al.

It is certified that error appears in the above-identified patent and that said Letters Patent is hereby corrected as shown below:

Title page,
Item [57] ABSTRACT,
Line 2, the word "1-dichloro-2,4-dinitrobenzene" should be replaced with -- 1-chloro-2,4-dinitrobenzene --.

Column 2,
Line 60, the word "1-dichloro-2,4-dinitrobenzene" should be replaced with -- 1-chloro-2,4-dinitrobenzene --.

Column 3,
Line 22, the word "1-dichloro-2,4-dinitrobenzene" should be replaced with -- 1-chloro-2,4-dinitrobenzene --.

Column 5,
Line 18, a -- ) -- should be inserted after the word "etc" and before the word "and".

Column 11,
Line 47, the word "is" after the word "ionic" and before the word "aluminum" should be removed.

Signed and Sealed this

Seventh Day of December, 2004

JON W. DUDAS
*Director of the United States Patent and Trademark Office*

UNITED STATES PATENT AND TRADEMARK OFFICE
CERTIFICATE OF CORRECTION

PATENT NO.       : 6,761,900 B2
APPLICATION NO. : 10/080526
DATED            : July 13, 2004
INVENTOR(S)      : Jutaro Shudo et al.

It is certified that error appears in the above-identified patent and that said Letters Patent is hereby corrected as shown below:

In column 4, line 15, the word "1-chloro-2,4-nitrobenzene" should be replaced with -- 1-chloro-2,4-dinitrobenzene --.

Signed and Sealed this

Twenty-fifth Day of December, 2007

JON W. DUDAS
*Director of the United States Patent and Trademark Office*